US009895543B2

(12) United States Patent
Lian et al.

(10) Patent No.: US 9,895,543 B2
(45) Date of Patent: Feb. 20, 2018

(54) IMPLANTABLE PULSE GENERATOR SYSTEM FOR VAGAL NERVE STIMULATION

(71) Applicant: BIOTRONIK SE & Co. KG, Berlin (DE)

(72) Inventors: Jie Lian, Beaverton, OR (US); Lauren Kraiter, Tigard, OR (US); Alan Fryer, Portland, OR (US); Andrew B. Kibler, Lake Oswego, OR (US); Dirk Muessig, West Linn, OR (US); Larry Stotts, Tigard, OR (US); Warren Dabney, Lake Oswego, OR (US); Jeffrey A. von Arx, Lake Oswego, OR (US)

(73) Assignee: BIOTRONIK SE & Co. KG (DE)

( * ) Notice: Subject to any disclaimer, the term of this patent is extended or adjusted under 35 U.S.C. 154(b) by 15 days.

(21) Appl. No.: 14/962,065

(22) Filed: Dec. 8, 2015

(65) Prior Publication Data

US 2016/0175595 A1     Jun. 23, 2016

Related U.S. Application Data

(60) Provisional application No. 62/095,070, filed on Dec. 22, 2014.

(51) Int. Cl.
*A61N 1/36* (2006.01)
*A61N 1/05* (2006.01)

(52) U.S. Cl.
CPC ....... *A61N 1/36139* (2013.01); *A61N 1/0556* (2013.01); *A61N 1/36053* (2013.01); *A61N 1/36114* (2013.01)

(58) Field of Classification Search
CPC . A61N 1/0551; A61N 1/3605; A61N 1/36057
See application file for complete search history.

(56) References Cited

U.S. PATENT DOCUMENTS 7,778,703 B2    8/2010   Gross et al.
7,783,362 B2    8/2010   Whitehurst et al.
(Continued)

FOREIGN PATENT DOCUMENTS

EP     2 077 893 A1      7/2009
EP     2 316 525 A1      5/2011
WO     WO 2008/024557   2/2008

OTHER PUBLICATIONS

European Search Report, Appln. No./Patent No. 15199207.0-1666, May 3, 2016.
(Continued)

*Primary Examiner* — Michael Carey
*Assistant Examiner* — Natasha Patel
(74) *Attorney, Agent, or Firm* — Craig A. Dieschko, Esq.; DeWitt Ross & Stevens S.C.

(57) ABSTRACT

An implantable pulse generator system includes a stimulation unit delivering vagal nerve stimulation pulses, an activity sensor determining an exertion level of the user and generating a signal representing metabolic demand, an autonomic tone sensor determining an autonomic status of the user and generating a signal representing autonomic status, and a control unit in communication with the foregoing components, and which is adapted to control the stimulation unit depending on both the signal representing metabolic demand and the signal representing autonomic status.

22 Claims, 8 Drawing Sheets

(56) References Cited

U.S. PATENT DOCUMENTS

| | | | |
|---|---|---|---|
| 8,401,604 B2 | 3/2013 | Gerlitz | |
| 8,473,068 B2 | 6/2013 | Farazi | |
| 8,712,547 B2 | 3/2014 | Whitehurst et al. | |
| 2004/0254612 A1* | 12/2004 | Ezra | A61N 1/36114 607/5 |
| 2006/0206154 A1* | 9/2006 | Moffitt | A61N 1/3627 607/9 |
| 2008/0051839 A1 | 2/2008 | Libbus et al. | |
| 2008/0058872 A1 | 3/2008 | Brockway et al. | |
| 2009/0234406 A1* | 9/2009 | Shuros | A61N 1/3627 607/11 |
| 2011/0009914 A1 | 1/2011 | Brockway et al. | |
| 2012/0123494 A1 | 5/2012 | Libbus et al. | |
| 2012/0245656 A1 | 9/2012 | Brockway et al. | |
| 2013/0184773 A1 | 7/2013 | Libbus et al. | |
| 2013/0345776 A1 | 12/2013 | Libbus et al. | |
| 2014/0135863 A1* | 5/2014 | Libbus | A61N 1/36114 607/14 |
| 2014/0155949 A1 | 6/2014 | Libbus et al. | |
| 2014/0243929 A1 | 8/2014 | Brockway et al. | |

OTHER PUBLICATIONS

Henning, Robert J. et al. "Vagal nerve stimulation increases right ventricular contraction and relaxation and heart rate", Cardiovascular Research 32, 1996, 846-853.

* cited by examiner

IMPLANTABLE PULSE GENERATOR SYSTEM FOR VAGAL NERVE STIMULATION

CROSS-REFERENCE TO RELATED APPLICATIONS

This application claims priority under 35 USC §119(e) to U.S. Provisional Patent Application 62/095,070 filed Dec. 22, 2014, the entirety of which is incorporated by reference herein.

FIELD OF THE INVENTION

This document concerns an implantable pulse generator system for autonomic adaptive control of vagal nerve stimulation (VNS).

BACKGROUND OF THE INVENTION

Vagal nerve stimulation (VNS) systems and methods are disclosed in (for example) U.S. Pat. Nos. 7,778,703; 7,783,362; 8,401,604; 8,473,068; and 8,712,547, as well as U.S. published patent applications 2013/0184773 and 2014/0155949. See also Robert J. Henning et al. "Vagal nerve stimulation increases right ventricular contraction and relaxation and heart rate", Cardiovascular Research 32, 1996, 846-853.

SUMMARY OF THE INVENTION

The invention, which is defined by the claims set forth at the end of this document, involves an improved system for vagal nerve stimulation. In an exemplary version of the invention, an implantable pulse generator system includes a stimulation unit for generating a delivery of vagal nerve stimulation pulses; an activity sensor for determining an exertion level of a user and generating a signal representing metabolic demand (e.g., cardiovascular demand); at least one autonomic tone sensor for determining an autonomic status of a user and generating a signal representing autonomic status; and a control unit connected to the stimulation unit, the activity sensor, and the autonomic tone sensor, and that is adapted to control the stimulation unit depending on both the signal representing metabolic demand and the signal representing autonomic status.

The implantable pulse generator system can provide closed loop control of vagal nerve stimulation to achieve autonomic balance. The implantable pulse generator system enables adaptive control of vagal nerve stimulation (VNS) in order to achieve optimal balance between VNS and the patient's exertion level.

Closed loop control of vagal nerve stimulation (VNS) is useful to maximize the beneficial effects of heart failure treatment while minimizing the risk of severe sympathetic depression. On one hand, it is preferred to activate and/or enhance VNS intensity in order to lower a patient's resting sympathetic tone. On the other hand, it is important to limit and/or inhibit VNS in order to preserve an appropriate degree of sympathetic activation when the patient is engaging in physical or mental activities. However, maintaining the optimal balance between VNS and the patient's exertion level remains a technical challenge.

The implantable pulse generator system provides adaptive control of the delivery of vagal nerve stimulation (VNS) by adapting the VNS to both the autonomic status and cardiovascular demand of the patient. The implantable pulse generator includes at least one activity sensor for measuring the patient's exertion level and at least one autonomic tone sensor for detecting the autonomic status of the patient.

The implantable pulse generator is preferably adapted to be capable of inducing either an increase in vagal tone or an increase in sympathetic tone. The control unit of the implantable pulse generator system is therefore preferably adapted to control the stimulation unit to generate stimulation pulses having stimulation parameters that are configured to induce a VNS effect that is either an increase in vagal tone or an increase in sympathetic tone, depending on both the signal representing cardiovascular demand and the signal representing autonomic status.

The control unit and the stimulation unit of the implantable pulse generator system are also preferably adapted to alter the effect of VNS by adjusting stimulation parameters such as one or more of amplitude, pulse width, and pulse timing, and/or by varying the selection of the stimulating electrode(s) used by the vagal nerve stimulator. Selection of stimulating electrodes may cause preferential activation of sub-regions of the vagus nerve in close proximity to the selected electrode, or, depending on the electrode geometry, may cause unidirectional propagation of action potentials selectively in either the efferent or afferent direction, by use of electrode geometries familiar to those skilled in the art.

The response of each electrode or stimulation parameter set can be determined by characterization prior to or during therapy, and the results of characterization can be applied to the automatic adaptive control disclosed herein. Accordingly, it is preferred that the control unit be programmable.

Preferably, if the activity sensor indicates a patient is at rest but the sympathetic tone is elevated, then VNS is activated (or its intensity is increased) in order to enhance the vagal tone to achieve autonomic balance. Additionally or alternatively, if the activity sensor indicates the patient is involved in exertion activities but the sympathetic tone is suppressed, then VNS is adapted to decrease vagal tone or enhance sympathetic tone so that the patient is supported in physical or mental activities without artificially induced limitation on exertion.

It is therefore preferred if the control unit is adapted to control the stimulation unit to generate stimulation pulses having stimulation parameters that are configured to induce an increase in vagal tone if the metabolic demand-representing signal of the activity sensor indicates a low demand, and the autonomic status-representing signal of the autonomic tone sensor indicates that the sympathetic tone is elevated.

It is also preferred if the control unit is adapted to control the stimulation pulse unit to generate stimulation pulses having stimulation parameters that are configured to induce a decrease in vagal tone and/or an increase in sympathetic tone if the metabolic demand-representing signal of the activity sensor indicates an elevated metabolic demand, and if the autonomic status-representing signal of the autonomic tone sensor indicates that the sympathetic tone is suppressed.

The activity sensor for providing the metabolic demand-representing signal preferably includes at least one of an accelerometer, a CLS sensor (Closed Loop Stimulation sensor), a temperature sensor, a tissue oxygenation sensor, and/or a minute ventilation sensor. A CLS sensor has been shown to be able to measure both physical and mental exertion of a patient.

The CLS sensor and/or the minute ventilation sensor preferably include or are connected to an impedance determination unit that is configured to determine one or more of an intracardiac and a transthoracic impedance.

By means of such an impedance determination unit, it is possible to determine both an intracardiac impedance and a transthoracic impedance. Transthoracic impedance can be evaluated to determine a tidal volume (minute volume) and breathing rate (minute rate). Intracardiac impedance can be used to determine stroke volume, contractility, heart rate and further metrics of a heart.

The Closed Loop Stimulation (CLS) sensor is configured to determine a course of intracardiac impedance and to compare the course with a reference course and/or to determine a maximum of the first derivative of the course of intracardiac impedance.

The autonomic tone sensor is preferably configured to process intracardiac electrogram (IEGM) signals, and to determine one or more of the following metrics from the IEGM signals: intrinsic heart rate (HR), heart rate variability (HRV), intrinsic atrioventricular (AV) conduction time, QRS duration and/or P wave duration.

Alternatively or additionally, the autonomic tone sensor may be configured to process heart sound signals that reflect contraction-induced pressure waves, intra-cardiac pressure and/or an impedance signal reflecting myocardial contractility.

Alternatively or additionally, the autonomic tone sensor may be configured to process nerve signals that reflect the patient's intrinsic nerve activity. The intrinsic nerve sensing could be near the site of stimulation or at a different nerve site. Target neurologic locations include (but are not limited to) the stellate ganglion, vagus nerve, or medulla oblongata.

Alternatively or additionally, the autonomic tone sensor may be configured to process signals that reflect the patient's state of blood pressure, vasodilatation and/or vasoconstriction.

Thus, the autonomic tone sensor measures a physiological signal that is known to be affected by the autonomic status. For example, the device can use IEGM sensing electrodes to measure the intrinsic heart rate (HR), which is directly modulated by the autonomic status of the patient. Elevated sympathetic tone leads to an increase in HR and vice versa. As another example, the intrinsic AV conduction time is known to be affected by the autonomic status of the patient. Elevated sympathetic tone is associated with decrease in intrinsic AV conduction time and vice versa. Another measure of autonomic tone could be achieved by measuring the delay from beginning of the electrical QRS signal to a vibration pulse measured at the cervical level via an accelerometer which is attached or adjacent to a VNS cuff. Such vibration pulse reflects a local change of blood pressure that is caused in a cervical blood vessel by myocardial contraction of the heart. The delay between the QRS signal and the vibration pulse is related to cardiac contractility, and the current autonomic state relative to a previous autonomic state may be derived. Other physiological parameters can also be measured for the evaluation of autonomic status, including but not limited to heart rate variability, QRS duration, P wave duration, heart sound (contraction-induced pressure waves), intra-cardiac pressure, etc.

A natural contraction of a heart chamber can be similarly detected by the evaluating electrical signals sensed by the sensing channels. In the sensed electrical signal the depolarization of atrial muscle tissue is manifested by occurrence of a P-wave. Similarly, the depolarization of ventricular muscle tissue is manifested by the occurrence of a R-wave. The detection of a P-wave or an R-wave signifies the occurrence of intrinsic atrial (As) or ventricular (Vs) events, respectively. The AV-delay is the time period between an atrial event and a prescribed point in time of a ventricular event. The heart rate (HR) is inverse to the time period between consecutive ventricular events. The heart rate variability (HRV) is based on the distribution of heart rate intervals over a fixed period of time; high frequency variations in heart rate are mediated by parasympathetic tone, while low frequency variations in heart rate are influenced by both parasympathetic and sympathetic tone.

In a healthy heart, initiation of the cardiac cycle normally begins with depolarization of the sinoatrial (SA) node. This specialized structure is located in the upper portion of the right atrium wall and acts as a natural "pacemaker" of the heart. In a normal cardiac cycle and in response to the initiation of SA depolarization, the right atrium contracts and forces the blood that has accumulated therein into the ventricle. The natural stimulus causing the right atrium to contract is conducted to the right ventricle via the atrioventricular node (AV node) with a short natural delay, the atrioventricular delay (AV-delay). Thus, a short time after the right atrial contraction—a time sufficient to allow the bulk of the blood in the right atrium to flow through the one-way valve into the right ventricle—the right ventricle contracts, forcing the blood out of the right ventricle to body tissue. A typical time interval between contraction of the right atrium and contraction of the right ventricle might be 120 ms; a typical time interval between contraction of the right ventricle and the next contraction of the right atrium might be 800 ms. Thus, it is a right atrial contraction (A), followed a relatively short time thereafter by a right ventricle contraction (V), followed a relatively long time thereafter by the next right atrial contraction, that produces the desired AV synchrony. Where AV synchrony exists, the heart functions very efficiently as a pump in delivering life-sustaining blood to body tissue; where AV synchrony is absent, the heart functions as an inefficient pump (largely because the right ventricle is contracting when it is not filled with blood).

The invention also involves a method for vagal nerve stimulation including the steps of determining an exertion level indicating metabolic demand; determining an autonomic status level; and delivering nerve stimulation pulses depending on both the determined exertion level and the autonomic status level.

Preferably, nerve stimulation pulses having stimulation parameters that are configured to induce an increase in vagal tone are delivered if the signal representing cardiovascular demand of the activity sensor indicates a low demand, and the signal representing autonomic status of the autonomic tone sensor indicates that the sympathetic tone is elevated.

It is further preferred to deliver nerve stimulation pulses having stimulation parameters configured to induce a decrease in vagal tone and/or an increase in sympathetic tone if the signal representing cardiovascular demand of the activity sensor indicates an elevated cardiovascular demand, and if the signal representing autonomic status of the autonomic tone sensor indicates that the sympathetic tone is suppressed.

Further advantages, features, and objects of the invention will be apparent from the remainder of this document in conjunction with the associated drawings.

DETAILED DESCRIPTION OF EXEMPLARY VERSIONS OF THE INVENTION

Figure 1:
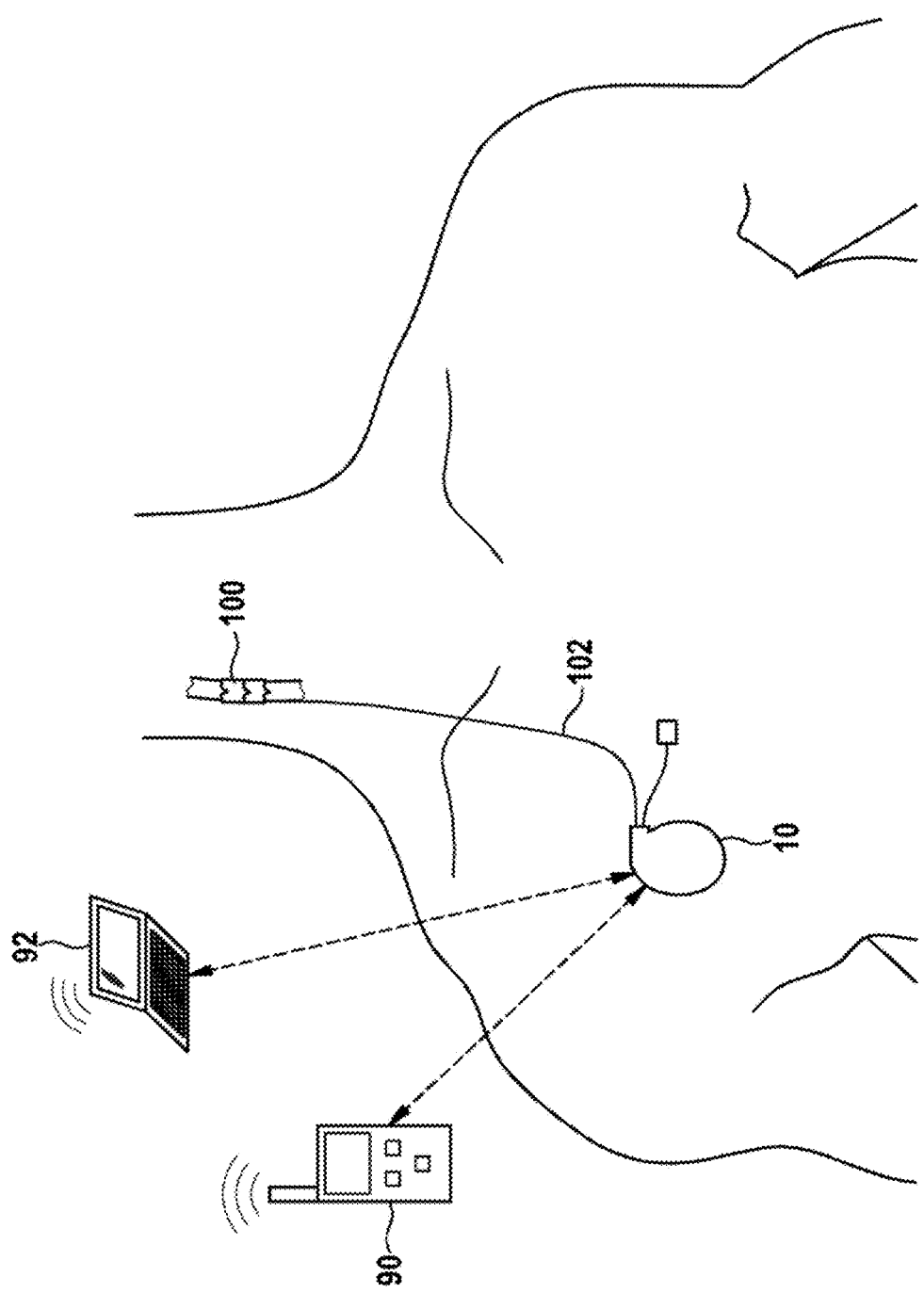
FIG. 1 illustrates a vagal nerve stimulation system.

FIG. 1 illustrates an implantable pulse generator system for vagal nerve stimulation. The system includes an implantable medical device 10, more specifically, an implantable pulse generator (IPG). The implantable medical device 10 is connected to a nerve stimulation electrode cuff 100 via a nerve stimulation electrode lead 102.

The implantable pulse generator 10 can be wirelessly programmed by an external programmer 92 via a MICS-band or similar wireless link. The implantable pulse generator 10 can also communicate with a bedside Patient Messenger 90 via a similar link. Arrhythmia detection, blood pressure waveform changes, and the other relevant diagnostic parameters can be transmitted to the bedside Patient Messenger 90, which can alert a Home Monitoring/Remote Programming Center if medical attention is required.

Figure 2:
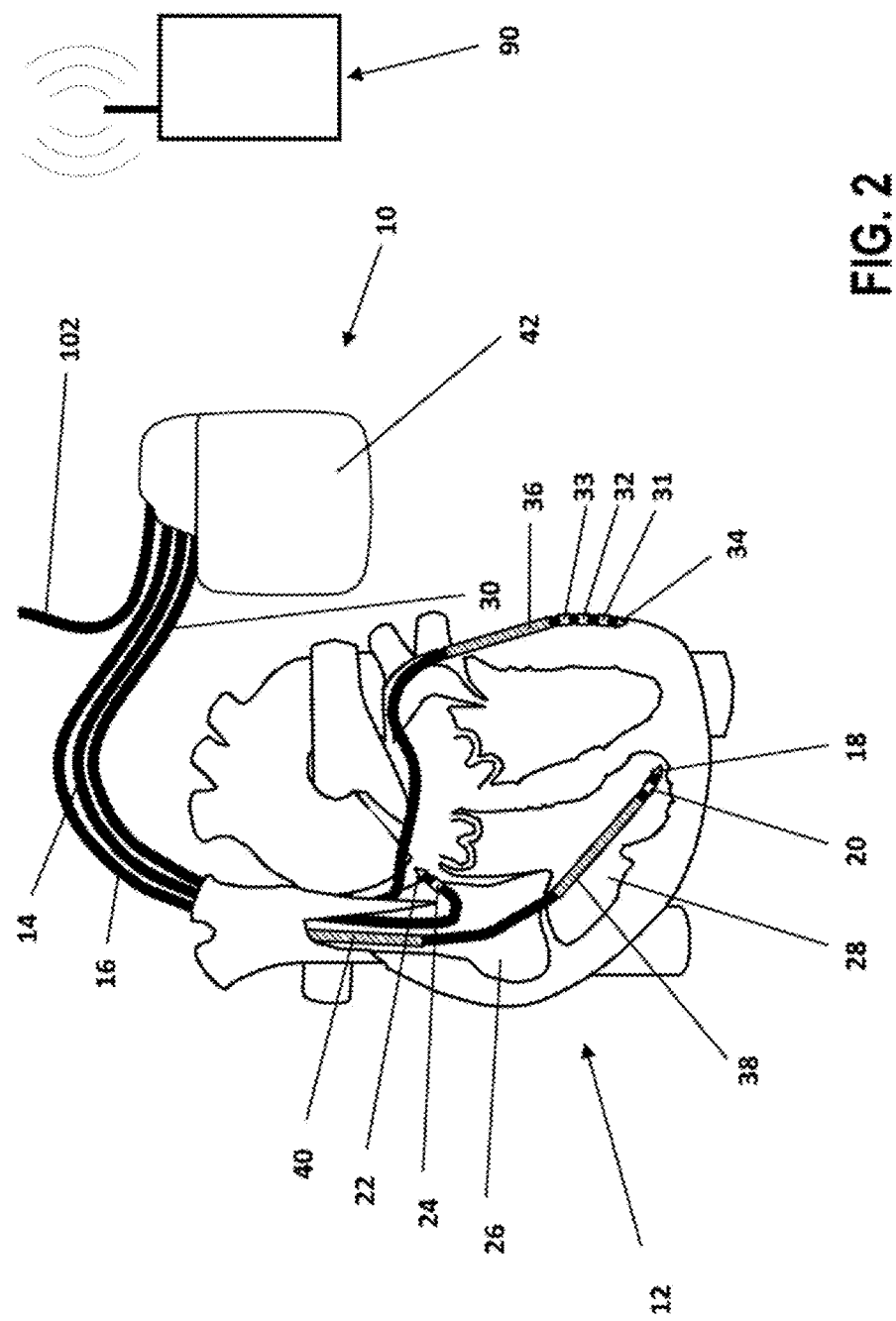
FIG. 2 illustrates an implantable pulse generator for heart stimulation and vagus stimulation.

In FIG. 2, the implantable medical device (IPG) 10 is a three chamber biventricular pacemaker and cardioverter/defibrillator that is connected to pacing/sensing leads placed in a heart 12. The implantable medical device 10 is additionally a vagal nerve stimulation pulse generator that is connected to cuff electrode 100 (FIG. 1) by means of nerve stimulation electrode lead 102.

The implantable medical device 10 is electrically coupled to heart 12 by way of leads 14, 16 and 30. Lead 14 is a right atrial electrode lead that has a pair of right atrial electrodes 22 and 24 that are in contact with the right atrium 26 of the heart 12. Lead 16 is a right ventricular electrode lead that has a pair of ventricular stimulation and sensing electrodes 18 and 20 that are in contact with the right ventricle 28 of heart 12. Further, a ventricular defibrillation shock coil 38 and an atrial defibrillation shock coil 40 are arranged on the right ventricular electrode lead 16.

Electrodes 22 and 18 are tip electrodes at the very distal end of leads 14 and 16, respectively. Electrode 22 is a right atrial tip (RA Tip) electrode and electrode 18 is a right ventricular tip (RV Tip) electrode. Electrodes 24 and 20 are ring electrodes in close proximity but electrically isolated from the respective tip electrodes 22 and 18. Electrode 24 forms a right atrial ring (RA Ring) electrode and electrode 20 forms a right ventricular ring (RV Ring) electrode. Atrial cardioversion shock coil 40 is a coil electrode providing a relatively large geometric area when compared to the stimulation electrodes 18, 20, 22 and 24.

Lead 30 is a left ventricular electrode lead passing through the coronary sinus of heart 12 and having left ventricular ring (LV Ring) electrodes 31, 32 and 33 and a left ventricular tip (LV Tip) electrode 34. A left ventricular defibrillation shock coil 36 is also provided on lead 30. It is noted that the number of left ventricular ring electrodes may vary depending on the electrode lead that is used, and throughout this document, it should be understood that discussions of one left ventricular ring electrode can be extended to additional left ventricular ring electrodes as well.

The implantable medical device 10 has a generator housing 42 made from electrically conductive material such as titanium that can serve as a large surface electrode (IMD Case). The various electrodes 18, 20, 22, 24, 31, 32, 33, 34, 36, 38 and 40 connected to the implantable medical device 10, together with the case 42, allow for a number of different electrode configurations for measuring intrathoracic and intracardiac impedance. For each intracardiac impedance measurement, a forcing function can be injected from a right ventricular ring electrode to a left ventricular ring electrode and a response function can be measured between the same electrodes (bipolar configuration; see FIG. 2), or a forcing function can be injected (and a response function measured) between a right ventricular tip electrode and a left ventricular tip electrode (quadripolar configuration; see FIG. 3). Further impedance measurement vectors resulting from different impedance measurement electrode combinations are possible.

Figure 3:
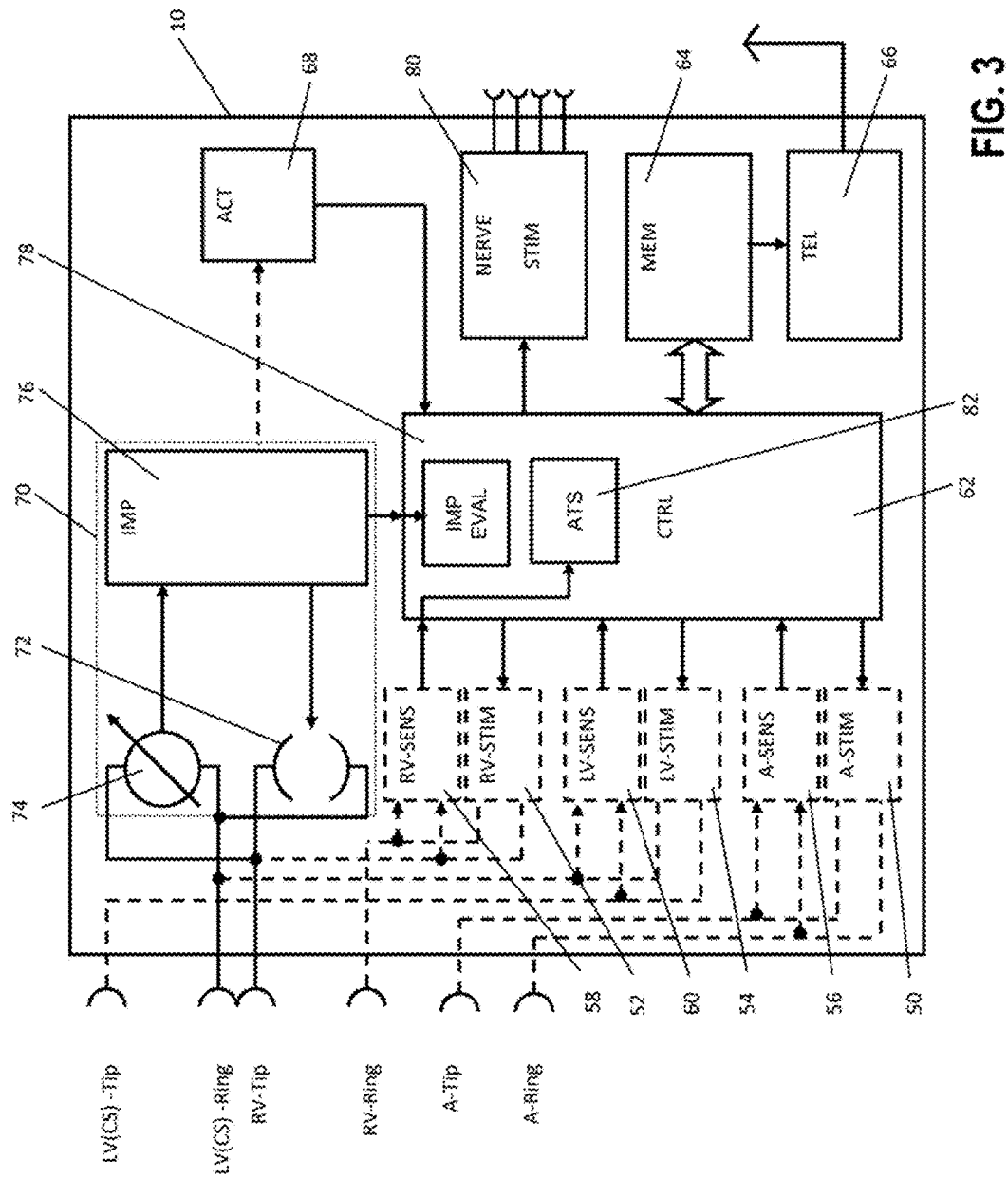
FIG. 3 is a schematic block diagram of an implantable pulse generator (IPG) used in the system of FIG. 1.
Figure 4:
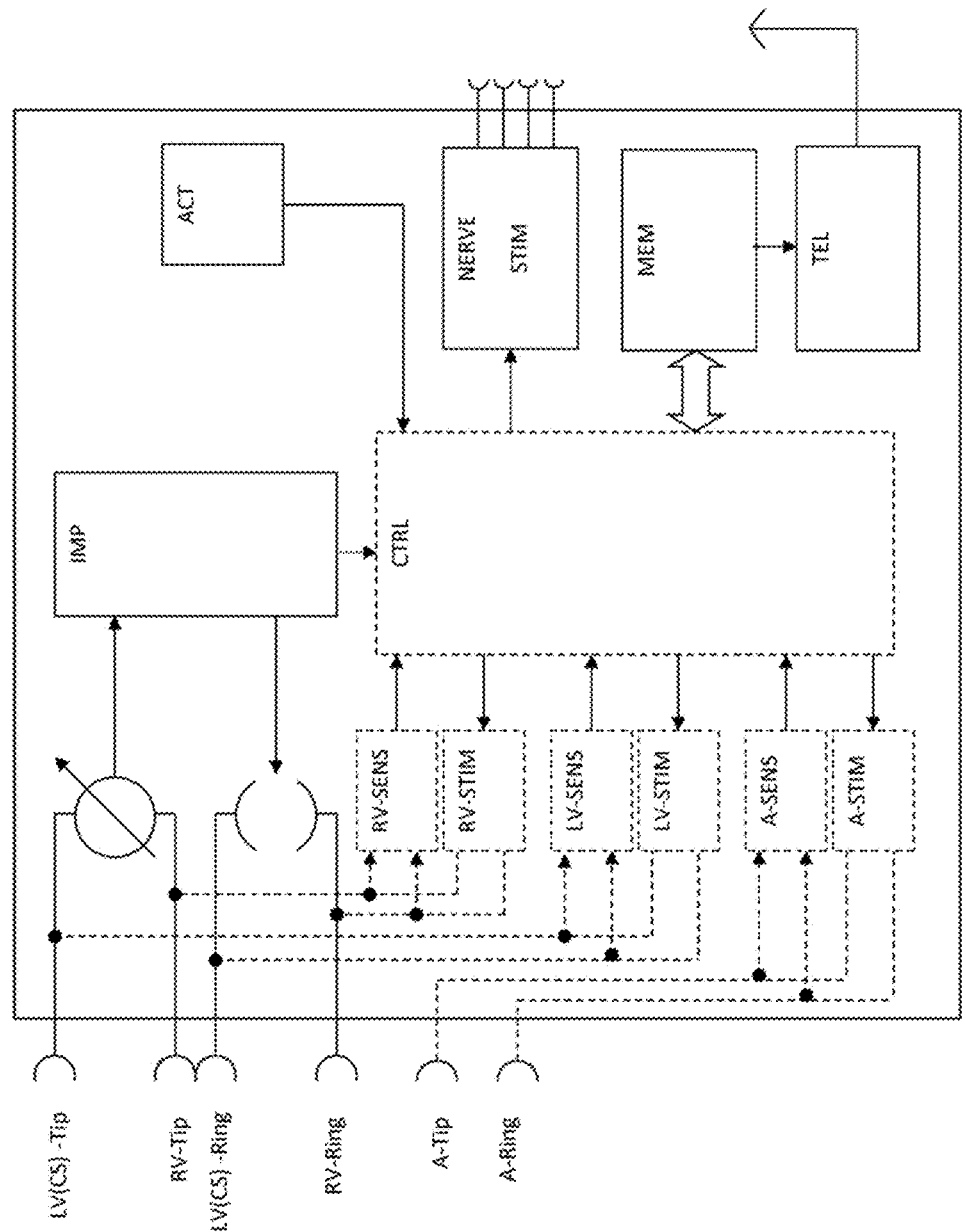
FIG. 4 is a schematic block diagram of an implantable pulse generator (IPG) used in the system of FIG. 1, showing an alternative electrode arrangement.

FIG. 3 depicts a simplified block diagram of an implantable medical device (pacemaker/defibrillator and neurostimulator) 10. During operation of the device 10, leads 14, 16 and 30 are connected to respective output/input terminals of device 10 as indicated in FIG. 2 and carry stimulating pulses to the tip electrodes 18, 22 and 34 from a right atrial stimulation pulse generator A-STIM 50, a right ventricular pulse generator RV-STIM 52, and a left ventricular pulse generator LV-STIM 54, respectively. Further, electrical signals from the right atrium are carried through the lead 14 from the electrode pair 22 and 24 to the input terminal of a right atrial channel sensing stage A-SENS 56, and electrical signals from the right ventricle are carried through the lead 16 from the electrode pair 18 and 20 to the input terminal of a right ventricular sensing stage RV-SENS 58. Likewise, electrical signals from the left ventricle are carried through the lead 30 from the electrode pair 32 and 34 to the input terminal of a left ventricular sensing stage LV-SENS 60.

A control unit CTRL 62 controls the implantable medical device 10, and is connected to sensing stages A-SENS 56, RV-SENS 58 and LV-SENS 60 and to stimulation pulse generators A-STIM 50, RV-STIM 52 and LV-STIM 54. Control unit CTRL 62 receives the output signals from the atrial sensing stage A-SENS 56, the right ventricular sensing stage RV-SENS 58, and the left ventricular sensing stage LV-SENS 60. The output signals of sensing stages A-SENS 56, RV-SENS 58 and LV-SENS 60 are generated each time that a P-wave representing an intrinsic atrial event, or an R-wave representing an intrinsic ventricular event, is sensed within the heart 12. An As signal is generated when the atrial sensing stage A-SENS 56 detects a P-wave, and a RVs signal is generated when the right ventricular sensing stage RV-SENS 58 detects an R-wave. These sense events As and RVs are used by control unit CTRL 62 as fiducial points of the respective intracardiac electrograms picked up by the sensing stages A-SENS 56, RV-SENS 58 and LV-SENS 60.

Control unit CTRL 62 also generates trigger signals that are sent to the atrial stimulation pulse generator A-STIM 50, the right ventricular stimulation pulse generator RV-STIM 52, and the left ventricular stimulation pulse generator LV-STIM 54. These trigger signals are generated each time that a stimulation pulse is to be generated by the respective pulse generator A-STIM 50, RV-STIM 52 or LV-STIM 54. The atrial trigger signal is referred to as the "A-pulse", and the ventricular trigger signals are referred to as the "RV-pulse" or the "LV-pulse." During the time that either an atrial stimulation pulse or ventricular stimulation pulse is being delivered to the heart, the corresponding sensing stage A-SENS 56, RV-SENS 58 and/or LV-SENS 60 is typically disabled by way of a blanking signal presented to these amplifiers from the control unit CTRL 62. This blanking action prevents the sensing stages A-SENS 56, RV-SENS 58 and LV-SENS 60 from becoming saturated from the relatively large stimulation pulses that are present at their input terminals during this time. This blanking action also helps prevent residual electrical signals present in the muscle tissue as a result of a stimulation pulse delivered from pacemaker 10 from being interpreted as P-waves or R-waves. Furthermore, an atrial sense event As recorded shortly after delivery of a ventricular stimulation pulses during a preset time interval, called the post-ventricular atrial refractory period (PVARP), is generally recorded as atrial refractory sense event Ars, but is ignored.

Control unit CTRL 62 includes circuitry for timing ventricular and/or atrial stimulation pulses according to an adequate stimulation rate that can be adapted to a patient's hemodynamic need, as discussed below. Control unit CTRL 62 includes an autonomic tone sensor 82 that is connected to the right ventricular sensing stage 58. The autonomic tone sensor 82 is configured to process intracardiac electrogram (IEGM) signals, and is preferably adapted to determine one or more of the following metrics from IEGM signals: intrinsic heart rate (HR), heart rate variability (HRV), intrinsic atrioventricular (AV) conduction time, QRS duration, and/or P wave duration.

Still referring to FIG. 3, the implantable medical device 10 includes a memory circuit MEM 64 that is coupled to the control unit CTRL 62 over a suitable data/address bus ADR. This memory circuit MEM 64 allows certain control parameters, used by the control unit CTRL 62 in controlling the operation of the implantable medical device 10, to be programmably stored and modified as required in order to customize the implantable medical device's operation to suit the needs of a particular patient. Such data includes the basic timing intervals used during operation of the pacemaker 10, and AV delay values and hysteresis AV delay values in particular. Further, data sensed during the operation of the implantable medical device 10 may be stored in the memory MEM 64 for later retrieval and analysis.

The implantable medical device 10 further includes a telemetry circuit TEL 66. This telemetry circuit TEL 66 is connected to the control unit CTRL 62 by way of a suitable command/data bus. Telemetry circuit TEL 66 allows for wireless data exchange between the implantable medical device 10 and some remote programming or analyzing device, which can (for example) be part of a centralized service center serving multiple pacemakers.

The implantable medical device 10 in FIG. 3 is referred to as a three chamber pacemaker/cardioverter/defibrillator because it interfaces with the right atrium 26, the right ventricle 28 and the left ventricle of the heart 12. Those portions of the pacemaker 10 that interface with the right atrium, e.g., the lead 14, the P-wave sensing stage A-SENSE 56, the atrial stimulation pulse generator A-STIM 50, and corresponding portions of the control unit CTRL 62, are commonly referred to as the atrial channel. Similarly, those portions of the pacemaker 10 that interface with the right ventricle 28, e.g., the lead 16, the R-wave sensing stage RV-SENSE 58, the ventricular stimulation pulse generator RV-STIM 52, and corresponding portions of the control unit CTRL 62, are commonly referred to as the ventricular channel.

In order to be able to determine a patient's metabolic demand, the pacemaker 10 further includes a physiological sensor ACT 68 that is connected to the control unit CTRL 62 of the pacemaker 10. While this sensor ACT 68 is illustrated in FIG. 3 as being included within the pacemaker 10, it should be understood that the sensor may also be external to the implantable medical device 10, yet still be implanted within or carried by the patient. A common type of activity sensor is an accelerometer, such as a micro electromechanical system (MEMS) accelerometer, mounted within the case 42 of the pacemaker 10. Other types of physiological sensors are also known, such as sensors that sense the oxygen content of blood, respiration rate, blood pH, intracardiac impedance changes, and the like. The invention is not limited to use with any one (or more) of the foregoing physiological sensors, and any sensor capable of sensing some physiological parameter relatable to physical activity and/or metabolic demand of a patient can be used. Such physiological sensors are commonly used with "rate-responsive" pacemakers in order to adjust the rate of the pacemaker in a manner that tracks the physiological needs of the patient. The output of sensor 68 represents an activity level.

In a typical version of the invention, the activity sensor 68 is an accelerometer. In an alternative version, the activity sensor 68 is the CLS sensor, which has been shown to be able to measure both physical and mental exertion of the patient. In yet another version of the invention, the activity sensor 68 is the minute ventilation sensor, which may be based on the measurement of the trans-thoracic impedance signal. With use of the output signal of the activity sensor 68, the control unit 62 is able to assign each intrinsic heart rate to an activity, thus enabling collection of separate intrinsic heart rate values for a patient's state of rest and a patient's state of exercise.

An impedance determination unit 70 is provided for impedance measurement. Impedance determination unit 70 includes a constant current source 72 that is connected or can be connected to electrodes for intracorporeal placement as shown in FIG. 1. In order to allow for different impedance measurement electrode configurations, preferably some means of switching is provided between the constant current source 72 and the electrode terminals of the implantable medical device 10. The switch is not shown in FIG. 2, and rather particular impedance measurement configurations are shown as examples.

Similarly, a voltage measuring unit 74 for measuring a voltage corresponding to a current fed through a body by the constant current source 72 is provided, and can be connected to different electrodes (though a switch for switching between these configurations is not shown in FIG. 2).

As an alternative to the constant current source 72, a constant voltage source can be provided to generate the forcing function. The measuring unit will then be adapted to measure a current strength of a current fed through a body by the constant voltage source.

Both constant current source 72 and voltage measurement unit 74 are connected to an impedance value determination unit 76 that is adapted to determine an impedance value for each measuring current pulse delivered by the constant current source 72. Further, an evaluation unit 78 is provided either as a separate unit or as part of control unit CTRL 62, as depicted in FIG. 2. The evaluation unit 78 is connected to the impedance determination unit 70 and is adapted to evaluate a sequence of consecutive impedance values determined by the impedance determination unit 70. The evaluation unit 78 includes a signal generator module (not shown) to construct the intracardiac impedance or conductance signal reflecting the time course of the impedance determination unit's output signal and its derivative, and also preferably includes a filter module (not shown) to filter the intracardiac impedance signal. The evaluation unit 78 is further connected to the right ventricular stimulation stage RV-STIM 52 and the right ventricular sensing stage RV-SENS 58 in order to receive signals representing cardiac events, namely right ventricular stimulation events RVp or right ventricular sense events RVs.

The constant current source 72 has its two poles connected to different connectors for different electrodes, for example (in FIGS. 2-3), the right ventricular ring electrode 20 and the left ventricular ring electrode 31, 32, or 33, or the left ventricular tip electrode 34 and the right ventricular tip electrode 18. The voltage measuring unit 74 has two poles connected to, for example, a connector for the left ventricular ring electrode 31, 32, or 33 and the right ventricular ring electrode 20, or to the left ventricular ring electrode 31, 32, or 33 and the right ventricular ring electrode 20. Thus, a bipolar or a quadripolar impedance measurement configuration is established.

Impedance measurement is carried out by injecting a constant measuring current and sampling the resulting voltage. The measuring current is preferably pulsed. Typically, the measuring current will feature biphasic pulses wherein two constant current pulses of opposite polarity form one pulse packet. A time gap is provided between two consecutive pulse packets, with the time gap being significantly longer than the duration of one pulse packet. The constant current pulses within each pulse packet have different polarities, but are each of the same intensity and of same duration. A typical value for the intensity of the constant current pulses is between 50 µA and 600 µA, and the typical pulse duration of a single constant current pulse is about 15 µs. The time gap between each two consecutive pulse packets may be 500 times longer than the duration of one constant current pulse. The two constant current pulses of opposite polarity within one pulse packet may not follow immediately each other but may have a time gap there between. This time gap however, will be very short compared to the time gap between two consecutive pulse packets. Furthermore, consecutive pulse packets may be face alternating such that a first pulse packet for example will begin with a positive constant current pulse whereas the following pulse packet will begin with a negative constant current pulse and end with a positive constant current pulse. Via intracardiac impedance measurement, the control unit 62 is able to determine a stroke volume, and/or a tidal volume and a ventilation rate (breathing rate) in a manner generally known to the skilled person.

The implantable pulse generator 10 further includes a nerve stimulation unit 80 for generating nerve stimulation pulses. The nerve stimulation unit 80 is connected to and controlled by control unit 62. When in use, nerve stimulation unit 80 is further connected to a nerve stimulation electrode lead which is preferably a quadripolar lead including four electric conductors connecting the nerve stimulation unit 80 to corresponding stimulation electrode poles of a nerve stimulation electrode cuff.

Figure 5:
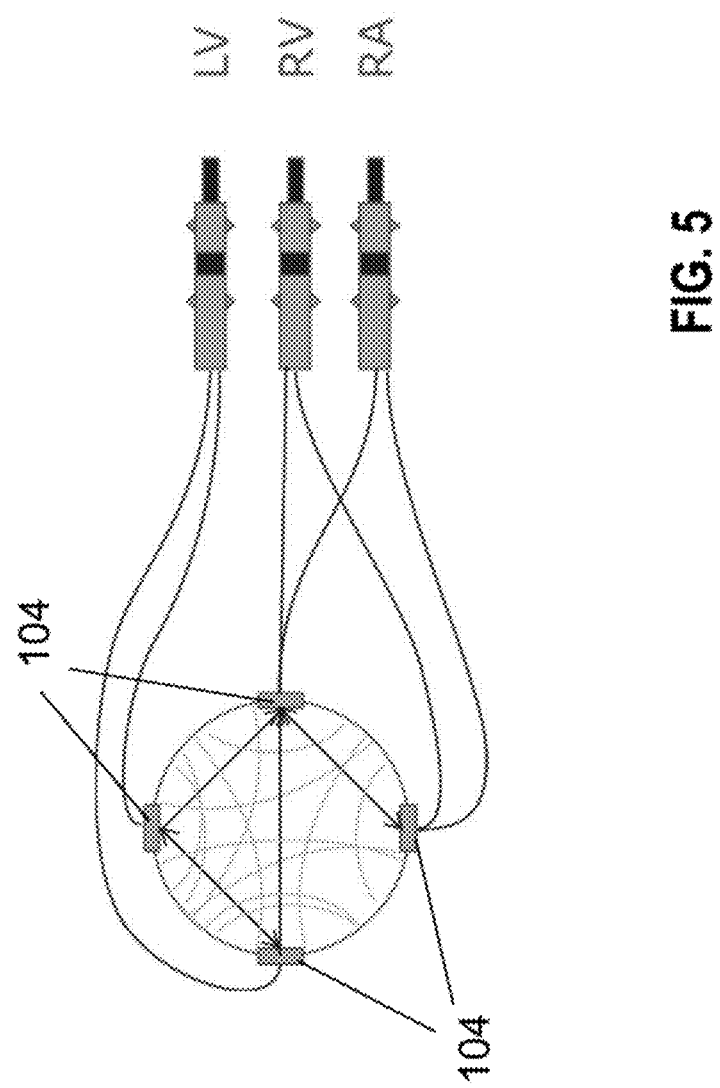
FIG. 5 is a schematic representation of a nerve stimulation electrode pole arrangement as used in the system of FIG. 1, arranged on a quadripolar stimulating cuff.

FIG. 5 discloses a nerve stimulation electrode pole arrangement as used in the system of FIG. 1. Four stimulation electrode poles 104 are arranged on the quadripolar stimulation electrode cuff 100. FIG. 5 further illustrates a cross-section of a nerve and stimulating vectors that can be achieved by means of electrode poles 104. The illustrated stimulation vectors are those used for obtaining the nerve stimulation results illustrated in FIG. 8.

In this arrangement, the autonomic tone sensor measures a physiological signal that is known to be affected by the autonomic status. For example, the device can use IEGM sensing electrodes to measure the intrinsic heart rate (HR) which is directly modulated by the autonomic status of the patient. Elevated sympathetic tone leads to increase in HR and vice versa. In another example, the intrinsic AV conduction time is known to be affected by the autonomic status of the patient. Elevated sympathetic tone is associated with decrease in intrinsic AV conduction time and vice versa. Another measure of autonomic tone could be achieved by measuring the delay from the beginning of the electrical QRS signal to a vibration pulse measured at the cervical level via an accelerometer attached or adjacent to a VNS cuff. The delay is related to cardiac contractility, and the current autonomic state relative to a previous autonomic state may be derived. Other physiological parameters can also be measured for the evaluation of autonomic status, including but not limited to heart rate variability, QRS duration, P wave duration, heart sound (contraction-induced pressure waves), intra-cardiac pressure, ganglionic and axonal nervous depolarization, etc.

A useful aspect of this invention arises from the discovery that it is possible to exert bimodal control of autonomic tone via a single stimulating cuff electrode implanted at the cervical vagus level. Although the vagus is understood by those skilled in the art to be primarily a parasympathetically active nerve, the cervical vagus contains a small percentage of sympathetically active fibers. The inventors have demonstrated that the action of these fibers may be selectively evoked via selection of stimulation parameters and by applying a multi-electrode nerve stimulation electrode cuff, allowing regional selectivity.

Figure 7:
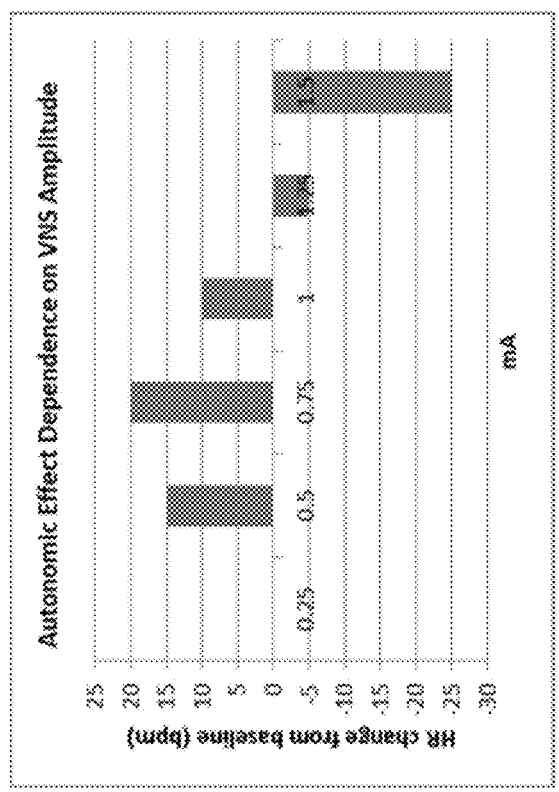
FIG. 7 illustrates experimental results demonstrating autonomic control (as evidenced by heart rate) modulated by a stimulation parameter, in this case VNS amplitude.
Figure 8:
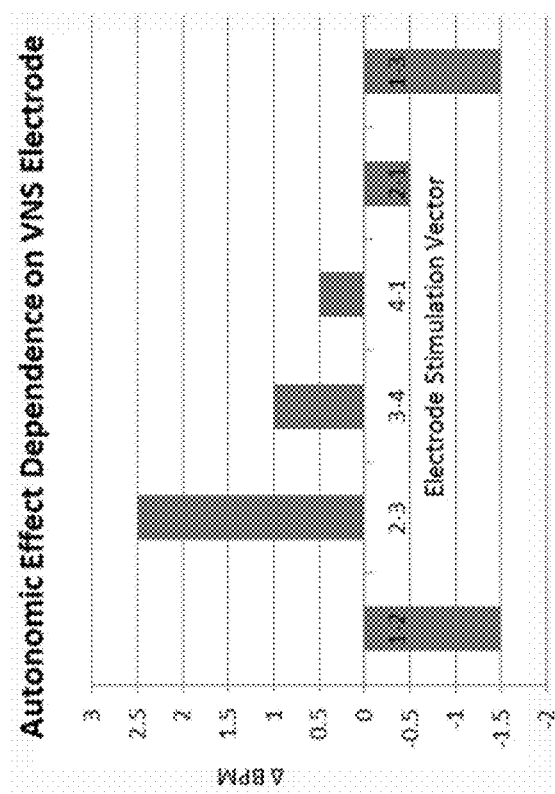
FIG. 8 illustrates experimental results demonstrating autonomic control (as evidenced by heart rate) modulated by electrode selection.

FIGS. 7 and 8 show experimental evidence of bimodal autonomic tone control via VNS. FIG. 7 depicts amplitude-based selective action of VNS seen in preclinical work, and FIG. 8 depicts stimulating electrode-based selectivity of VNS using a quadripolar stimulating electrode, shown in FIG. 5.

Three typical scenarios are illustrated below. In one example, the activity sensor indicates the patient's exertion level is low (e.g. sensor-indicated cardiovascular activity, such as heart rate, is low), but the measured intrinsic HR is high or the AV conduction time is short. This scenario suggests patient's sympathetic tone is high although patient is at rest. Thus VNS is activated or its intensity is increased to suppress the sympathetic activity. Intensity can be increased by increasing stimulation parameters such as amplitude, pulse width, or frequency and/or number of pulses delivered.

In another example, the activity sensor indicates patient's exertion level is increased (e.g. sensor-indicated activity level is high), but the measured intrinsic HR is low or the AV conduction time is long. This scenario suggests the suppression of sympathetic tone despite the patient's exertion. Thus VNS is deactivated or its intensity is reduced to relieve the sympathetic inhibition. In the scenario where modulation of VNS is controlled by a CLS signal, larger differential area between the CLS impedance waveform and the reference impedance waveform indicates higher feedback gain, which leads to greater adjustment of the VNS intensity. In the scenario where modulation of VNS is controlled by an accelerometer, a higher level of motion indicates higher feedback gain and greater adjustment of VNS intensity.

Intensity can be increased by increasing stimulation parameters such as amplitude, pulse width, or frequency and/or number of pulses delivered.

In a third example, a patient activity sensor including a motion sensor and/or CLS sensor determines that the patient's metabolic demand has increased but the measured HR is low or the AV conduction time is long. In addition, parasympathetic enhancement has via VNS has already been reduced or turned off. This scenario suggests that the patient may benefit from temporarily enhanced sympathetic tone to support metabolic function. Thus VNS is adapted to enhance sympathetic tone by a modification of stimulation parameters, as amplitude, pulse width, and/or pulse timing, or stimulation electrode of the VNS system which selectively activates a desired subset of vagal fibers, and/or the direction of propagation of the activation of desired fibers. Thus, the increased metabolic demand is positively supported by adaptation of VNS parameters.

Figure 6:
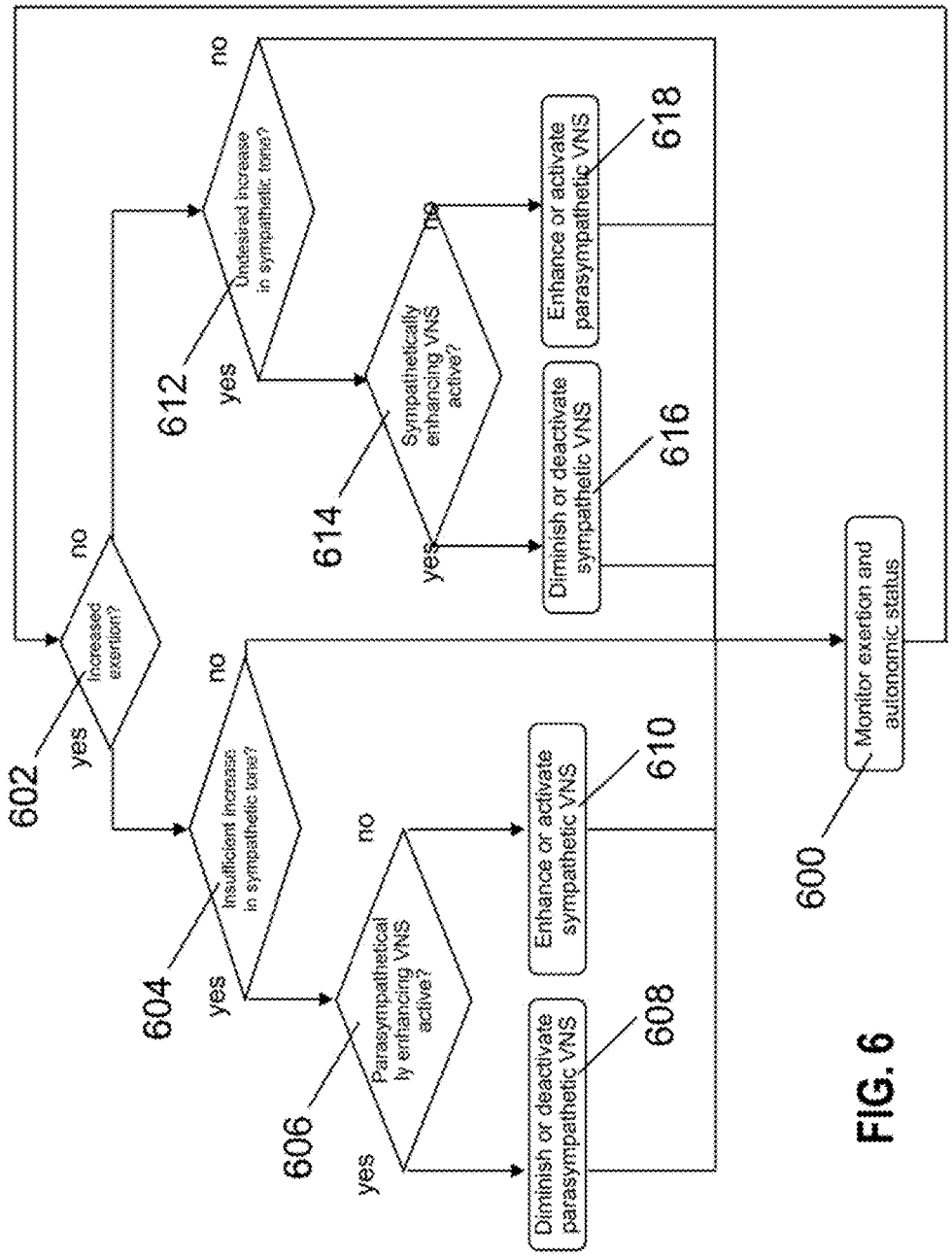
FIG. 6 is a high level flowchart illustrating the concept of adaptive closed-loop control of VNS.

The control unit 62 is adapted to control the nerve stimulation pulse generator 80 accordingly. Operation of the control unit 62 is illustrated by means of the flow diagram in FIG. 6. According to the flow chart in FIG. 6, the implantable pulse generator 10 monitors exertion and autonomic status (600). The implantable pulse generator 10 then decides whether or not exertion has increased (602), as by determining whether cardiovascular activity has increased. If exertion has increased, the implantable pulse generator 10 determines whether there is an insufficient increase in sympathetic tone (604). If that is the case, the implantable pulse generator 10 determines whether or not parasympathetically enhancing vagal nerve stimulation is active (606). Should that be the case, the implantable pulse generator 10 controls nerve stimulation unit 80 so as to diminish or to deactivate parasympathetic vagal nerve stimulation (608). Alternatively, if parasympathetically enhancing vagal nerve stimulation is not active, the implantable pulse generator 10 controls the nerve stimulation unit 80 so as to enhance or activate sympathetic vagal nerve stimulation (610). If there is sufficient increase in sympathetic tone (604), the implantable pulse generator 10 returns to monitoring exertion and autonomic status (600).

In case the implantable pulse generator 10 determines there is no increased exertion (602), the implantable pulse generator 10 further determines whether or not there is an undesired increase in sympathetic tone (612). Should that be the case, the implantable pulse generator further determines whether or not sympathetically enhancing vagal nerve stimulation is active (614). If it is active, the implantable pulse generator 10 controls the nerve stimulation unit 80 so as to diminish or deactivate sympathetic vagal nerve stimulation (616). Otherwise, the implantable pulse generator 10 controls the nerve stimulation unit 80 so as to enhance or activate parasympathetic vagal nerve stimulation (618).

If the implantable pulse generator 10 determines that there is no increased exertion and there is no undesired increase in sympathetic tone, the implantable pulse generator 10 returns to monitoring exertion and autonomic status (600).

The invention's closed-loop control of VNS offers a unique solution to a challenging problem, and optimally balances the VNS and cardiovascular exertion via bimodal control of autonomic tone via VNS. Rather than using a CLS impedance signal to adjust pacing rate, the invention uses this signal as feedback to modulate the VNS, thus offering a different way to close the gap of the autonomic control loop, which is often compromised in heart failure patients.

It should be understood that the versions of the invention described above are merely exemplary, and the invention is not intended to be limited to these versions. Rather, the scope of rights to the invention is limited only by the claims set out below, and the invention encompasses all different versions that fall literally or equivalently within the scope of these claims.

What is claimed is:

1. An implantable pulse generator system including:
    a. a nerve stimulation cuff electrode having at least one nerve stimulation electrode pole;
    b. a nerve stimulation unit configured to deliver vagal nerve stimulation pulses;
    c. an activity sensor configured to generate a signal representing a patient's exertion level;
    d. an autonomic tone sensor configured to generate a signal representing the patient's autonomic status; and
    e. a control unit:
        (1) in communication with the nerve stimulation unit, the activity sensor, and the autonomic tone sensor, and
        (2) configured to control the nerve stimulation unit to generate stimulation pulses having stimulation parameters configured to induce a vagus nerve stimulation (VNS) effect that is at least one of:
            A. a decrease in vagal tone, or
            B. an increase in sympathetic tone,
        when:
            i. the signal representing exertion level indicates elevated exertion, and
            ii. the signal representing autonomic status indicates a suppressed sympathetic tone.

2. The implantable pulse generator system of claim 1 wherein the control unit and the nerve stimulation unit are configured to alter the effect of VNS by adjusting stimulation parameters, wherein the stimulation parameters include at least one of:
    a. stimulation pulse amplitude,
    b. stimulation pulse width,
    c. stimulation pulse timing, and
    d. selection of stimulating electrodes.

3. The implantable pulse generator system of claim 1 wherein the control unit is further configured to control the nerve stimulation unit to generate stimulation pulses having stimulation parameters configured to induce an increase in vagal tone if:
    a. the signal representing the patient's exertion level indicates low exertion, and
    b. the signal representing autonomic status indicates an elevated sympathetic tone.

4. The implantable pulse generator system of claim 3 wherein:
    a. the signal representing autonomic status includes at least one of:
        (1) intrinsic heart rate (HR),
        (2) intrinsic atrioventricular conduction time (AV),
        (3) heart rate variability (HRV),
        (4) QRS duration, and
        (5) P wave duration, and
    b. elevated sympathetic tone is indicated when at least one of:
        (1) intrinsic heart rate (HR) is high,
        (2) intrinsic atrioventricular conduction time (AV) is low,
        (3) heart rate variability (HRV) is high,
        (4) QRS duration is low, and
        (5) P wave duration is low.

5. The implantable pulse generator system of claim 1 wherein the activity sensor includes an accelerometer.

6. The implantable pulse generator system of claim 1 wherein the activity sensor includes a closed loop stimulation (CLS) sensor.

7. The implantable pulse generator system of claim 1 wherein the activity sensor includes at least one of:
   a. a minute ventilation sensor,
   b. a temperature sensor,
   c. a tissue oxygenation sensor,
   d. a sensor configured to process nerve signals that reflect the patient's intrinsic nerve activity, and
   e. a sensor configured to process signals that reflect the patient's blood pressure.

8. The implantable pulse generator system of claim 1 wherein the autonomic tone sensor is configured to process IEGM signals.

9. The implantable pulse generator system of claim 1 wherein the cuff electrode has two or more nerve stimulation electrode poles.

10. The implantable pulse generator system of claim 1 further including:
    a. a generator housing containing the control unit and the nerve stimulation unit;
    b. a nerve stimulation electrode lead extending between the generator housing and the cuff electrode, wherein the nerve stimulation electrode lead electrically connects the nerve stimulation unit to the nerve stimulation electrode pole.

11. The implantable pulse generator system of claim 10:
    a. further including a heart pacing/sensing lead extending from the generator housing, the heart pacing/sensing lead having a cardiac electrode configured to sense IEGM signals; and
    b. wherein the autonomic tone sensor is configured to process IEGM signals sensed at the cardiac electrode.

12. The implantable pulse generator system of claim 11 wherein:
    a. the autonomic tone sensor is configured to process IEGM signals to derive at least a portion of the signal representing the patient's autonomic status, and
    b. the signal representing the patient's autonomic status includes at least one of:
       (1) intrinsic heart rate (HR),
       (2) intrinsic atrioventricular conduction time (AV),
       (3) heart rate variability (HRV),
       (4) QRS duration, and
       (5) P wave duration.

13. The implantable pulse generator system of claim 1:
    a. wherein the nerve stimulation cuff has two or more nerve stimulation electrode poles, wherein the nerve stimulation unit delivers the vagal nerve stimulation pulses via the cuff electrode; and
    b. wherein the control unit is further configured to adapt the stimulation parameters of the stimulation pulses to selectively stimulate:
       (1) primarily parasympathetic nerve fibers while avoiding stimulation of primarily sympathetic nerve fibers, and
       (2) primarily sympathetic nerve fibers fibers while avoiding stimulation of primarily parasympathetic nerve fibers.

14. A method for vagal nerve stimulation, the method including the steps of:
    a. determining an exertion level of a patient via an activity sensor;
    b. determining an autonomic status level of the patient via an autonomic tone sensor;
    c. delivering nerve stimulation pulses via a nerve stimulation unit, the pulses:
       (1) being delivered in dependence on the determined exertion level and the determined autonomic status level, and
       (2) having stimulation parameters configured to induce at least one of:
          A. a decrease in vagal tone, and
          B. an increase in sympathetic tone,
          when:
          i. the signal representing exertion level indicates elevated exertion, and
          ii. the signal representing autonomic status indicates a suppressed sympathetic tone.

15. The method of claim 14 further including the step of delivering nerve stimulation pulses having stimulation parameters configured to induce an increase in vagal tone if:
    a. the signal representing the patient's exertion level indicates low exertion, and
    b. the signal representing autonomic status indicates an elevated sympathetic tone.

16. The method of claim 14 further including the step of adapting the stimulation pulses whereby they selectively stimulate:
    (1) primarily parasympathetic nerve fibers while avoiding stimulation of primarily sympathetic nerve fibers, and
    (2) primarily sympathetic nerve fibers while avoiding stimulation of primarily parasympathetic nerve fibers.

17. The method of claim 16 wherein the nerve stimulation pulses are delivered via a cuff electrode.

18. The method of claim 17 wherein the cuff electrode includes two or more nerve stimulation electrode poles.

19. The method of claim 14 further including the step of determining the autonomic status level of the patient by processing IEGM signals captured by the autonomic tone sensor.

20. The method of claim 14 wherein the activity sensor is a closed loop stimulation (CLS) sensor.

21. An implantable pulse generator system including:
    a. a generator housing;
    b. a nerve stimulation electrode lead extending between the generator housing and a cuff electrode;
    c. a nerve stimulation unit within the housing, the nerve stimulation unit being configured to deliver vagal nerve stimulation pulses to the cuff electrode via the nerve stimulation electrode lead;
    d. a heart pacing/sensing lead extending from the generator housing, the heart pacing/sensing lead having a cardiac electrode configured to sense IEGM signals;
    e. an autonomic tone sensor within the housing, the autonomic tone sensor being configured to process the sensed IEGM signals and derive a signal representing the patient's autonomic status therefrom;
    f. an activity sensor configured to generate a signal representing a patient's exertion level;
    wherein the nerve stimulation unit is further configured to deliver to the cuff electrode vagal nerve stimulation pulses having stimulation parameters configured to induce:
    (1) an increase in vagal tone when:
       A. the signal representing the patient's exertion level indicates low exertion, and
       B. the signal representing autonomic status indicates an elevated sympathetic tone; and
    (2) a decrease in vagal tone when:
       A. the signal representing the patient's exertion level indicates elevated exertion, and B. the signal representing autonomic status indicates a suppressed sympathetic tone.

22. The implantable pulse generator system of claim 21 wherein the activity sensor is a closed loop stimulation (CLS) sensor.

* * * * *